United States Patent [19]

Jessop

[11] 4,303,611

[45] Dec. 1, 1981

[54] ANALYZER APPARATUS FEATURING A SIMPLIFIED INCUBATOR

[75] Inventor: Thomas C. Jessop, Webster, N.Y.

[73] Assignee: Eastman Kodak Company, Rochester, N.Y.

[21] Appl. No.: 177,050

[22] Filed: Aug. 11, 1980

[51] Int. Cl.³ ............................................. G01N 35/04
[52] U.S. Cl. ........................................ 422/65; 422/63; 422/104; 119/35
[58] Field of Search ....................... 422/63, 64, 65, 66, 422/104; 119/35

[56] References Cited

U.S. PATENT DOCUMENTS

| | | | |
|---|---|---|---|
| 3,533,744 | 10/1970 | Unger | 422/65 X |
| 3,556,731 | 1/1971 | Martin | 422/65 |
| 3,562,114 | 2/1971 | Steidl et al. | |
| 3,728,227 | 4/1973 | Elson et al. | |
| 4,029,419 | 6/1977 | Schumann, Jr. et al. | |
| 4,047,032 | 9/1977 | Judge et al. | |
| 4,056,358 | 11/1977 | Priarone et al. | |
| 4,066,403 | 1/1978 | Bruschi | |
| 4,118,280 | 10/1978 | Charles et al. | |
| 4,152,390 | 5/1979 | Nosco et al. | |

OTHER PUBLICATIONS

*Research Disclosure,* vol. 161, Pub. No. 16104, Sep. 1977, vol. 176, Pub. No. 17654, Dec. 1978.

*Primary Examiner*—Ronald Serwin
*Attorney, Agent, or Firm*—Dana M. Schmidt

[57] ABSTRACT

An analyzer apparatus and a method of analyte detection are disclosed, the apparatus featuring an incubator and detecting means. The incubator is designed to guide a sequence of test elements therethrough while each element is in contact with adjacent elements. Optional means are included for urging the elements to move through the incubator to the detecting means.

20 Claims, 10 Drawing Figures

ANALYZER APPARATUS FEATURING A SIMPLIFIED INCUBATOR

FIELD OF THE INVENTION

This invention relates to apparatus and a detection method particularly adapted for the chemical analysis of substances, known as analytes, in liquids.

BACKGROUND OF THE INVENTION

Numerous radiometric analyzers of blood have been disclosed, most of which involve fairly complex apparatus designed to provide automated handling of blood samples and test elements. Such handling usually included metering of samples onto the elements, incubation and detection of the resulting radiometric changes. Examples of such analyzers are described in, e.g., U.S. Pat. No. 4,152,390, issued on May 1, 1979.

To obtain a productive through-put rate, it is desirable that such analyzers accommodate a backlog of the test elements. Usually the backlog is temporarily stored in the incubator during the development stage. Some analyzers feature rotating circular incubators which involve the following complexities: Unless complicated equipment is added to load the incubator without stopping it, such incubators must include motors, gearing and the like to stop the incubator for loading and unloading, and to restart it. So that test elements can be loaded in any position that becomes available in the incubator, each element's location at a specific "address" in the rotating incubator must be "remembered," entailing computer tracking of the element for proper retrieval of the element and reloading of the incubator. Since the load station is fixed relative to the rotating incubator, access to the incubator is limited to those instances when an empty incubator position appears at the load station. Finally, an incubator that rotates with respect to the remaining apparatus must provide temperature control through a coupling system that accommodates relative movement, e.g., electric slip rings. Although all these aspects of the rotating incubator are well within the skill of the art, they increase the cost and complexity of the incubator, and weigh against on-site analysis, e.g., at the physician's office.

A further difficulty in designing such incubators occurs because certain test chemistries produce gases which, if carried over to the following test samples, would cause erroneous readings. For example, test elements that quantify levels of BUN usually produce ammonia. Examples of such test elements are described in U.S. Pat. No. 4,066,403, issued on Jan. 3, 1978. Ammonia that is intended to create a color change only internally in its test element can escape, in some instances. In the worst case, this gas is carried as a contaminant to the next test element in an incubator. At best, escaping gas represents analyte that will not be detected, possibly resulting in a low reading. Prior to this invention, the problem of contamination from escaping gas has been dealt with through the use of test element covers and incubator materials that absorb little of the gas in question.

SUMMARY OF THE INVENTION

This invention is directed to apparatus for the analysis of liquids, a simplified incubator therefor, and a method of detecting analytes, that are capable of a productive through-put rate without the problems outlined above.

More specifically, in one aspect of the invention there is provided an incubator for apparatus that detects sample analyte responses in generally flat test elements having a first major surface that includes a sample-containing portion, and one or more opposing support surfaces. The incubator includes wall means for (a) defining a path between first and second locations and (b) supporting the elements for movement along the path with each element in contact with the adjacent elements and with the sample-containing portion of all but one element covered by the opposing support surfaces of an adjacent element. Optionally, the incubator further includes means for maintaining the incubator at a predetermined temperature.

In another aspect of the invention, there is provided apparatus that includes the above-described incubator, means for loading test elements into the incubator at the above-noted first location, means for unloading the test elements from the incubator at the second location, and means adjacent the second location for detecting the detectable response of the test elements.

In a further aspect of the invention, the incubator comprises wall means defining a stationary, generally elongated chamber and at the above-noted first location, an access aperture permitting introduction of elements into the chamber, the chamber being adapted to support a plurality of the test elements in a configuration wherein each element is in contact with adjacent elements.

In yet another aspect of the invention, the incubator includes guide means for guiding a plurality of such test elements in succession from the first location to the second location with the surfaces of adjacent elements in an opposed, contacting relation; loading means being disposed to orient elements in the guide means such that the sample-containing portion of all but one element is covered by the opposing surfaces of an adjacent element.

The method of the invention provides detection of analytes by sequentially placing test elements containing the sample liquid, into a configuration wherein each element is in contact with adjacent elements and the sample-containing portion of all but one of the elements is covered by one or more support surfaces of one of the adjacent elements, detecting a response in the elements in the same sequence as they are placed in the configuration, and removing the test elements from the configuration either before or after the detection step.

Thus, one advantage of the present invention is that an analyzer is provided with a high through-put, "time-independant access" incubator that does not require the motors and controls of rotating incubators. Preferably this is achieved by making the incubator stationary with respect to the rest of the analyzer.

A related advantage of the invention is that an analyzer is provided with an incubator that avoids the necessity for sophisticated addressing systems to recall the patient identity associated with each of several incubator locations.

Another advantage of the invention is that an analyzer incubator is provided that arranges the test elements so that the elements themselves function to prevent gas escape such as would cause a low reading or a gas crossover or contamination from one element to another.

Still another advantage of the invention is that the incubator of the analyzer is drastically reduced in size.

DESCRIPTION OF THE PREFERRED EMBODIMENTS

Figure 1:
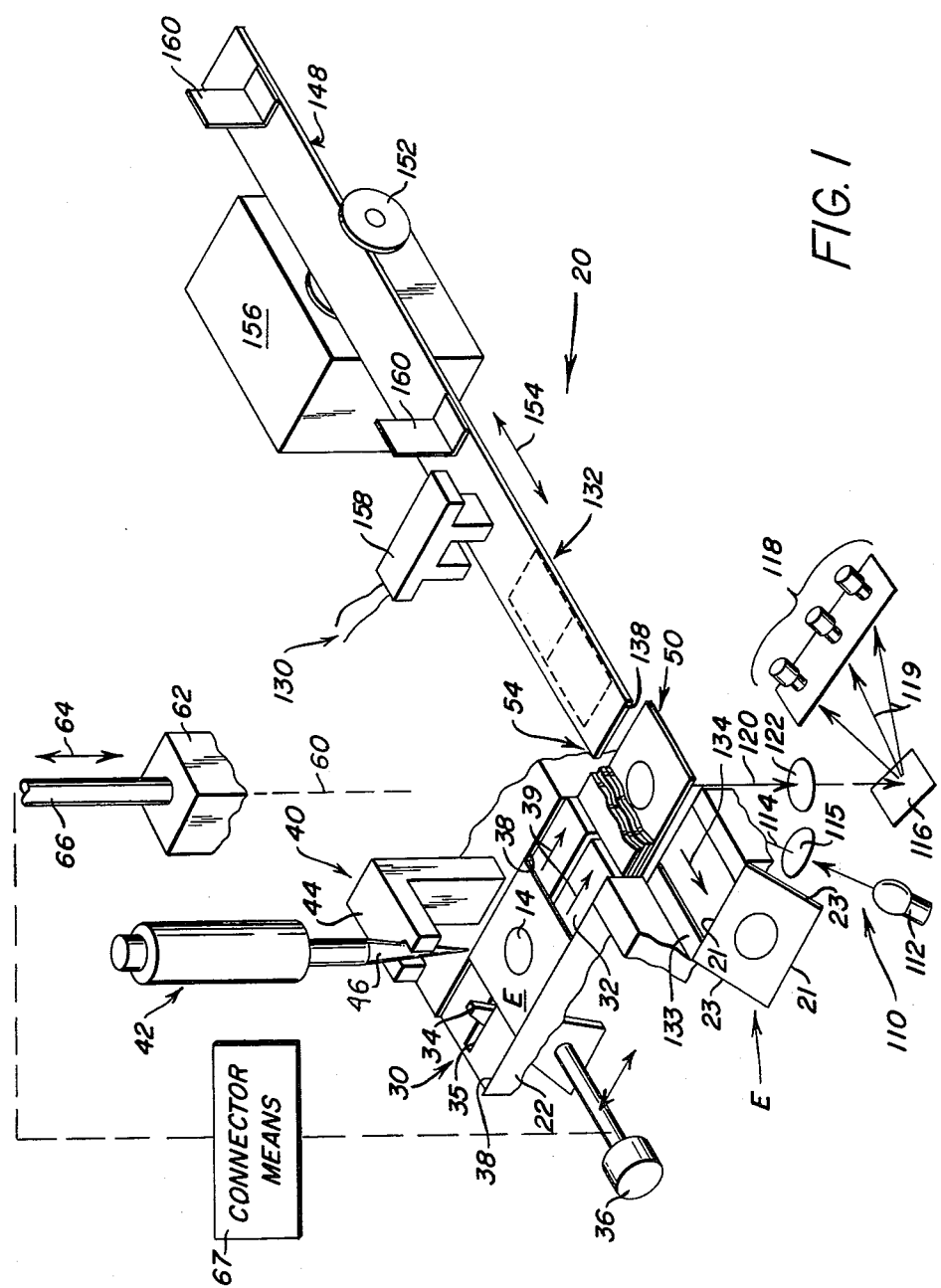
FIG. 1 is a fragmentary, partially schematic, partially broken away perspective view of an analyzer constructed in accordance with the invention.

The incubator of this invention is capable of measuring a variety of analytes of liquids, particularly those of biological liquids. This is accomplished conveniently through the use of generally flat test elements E and E', FIG. 3, that feature a first major surface defined by a sample-containing portion 14 mounted in a plastic frame member 15. Portion 14 in turn comprises one or more absorbent layers 17 on a transparent support 14'. The top surface of layers 17 is exposed to receive a quantity of liquid, such as a drop shown in dotted outline, FIG. 3. Opposite to the layers of portion 14 are the support surfaces of the element, comprising the bottom surface 16 of frame member 15, and the bottom surface 19 of support 14' exposed through window 18 of frame member 15.

In an alternative embodiment, support surfaces 16 and 19 are all one surface (not shown) formed as a single unitary support wherein the support 14' is an extension of frame member 15.

The structure of layers 17 permits them to contain liquid that is deposited thereon. Layers 17 preferably are constructed in the manner described in U.S. Pat. Nos. 3,992,158, issued Nov. 16, 1976, and 4,066,403, issued Jan. 3, 1978, the details of which are expressly incorporated herein by reference. Deposited liquid spreads into the layers where the reaction takes place that generates a detectable change.

Side edges 21 and 23, FIG. 1, define the width and length, respectively, of the elements. Such dimensions are subject to variation, as desired. The thickness of the various layers of elements E has been exaggerated for clarity in FIG. 3. In practice, the total thickness of element E is only about 1 mm.

U.S. Pat. No. 4,169,751, issued on Oct. 2, 1979, discloses a fully comparable and useful test element wherein test portion 14 is staked to a support frame apertured to allow a liquid drop to permeate into portion 14. The disclosed details of the element of that patent are incorporated herein by reference.

Elements such as elements E and E' are preferably processed by spotting with a drop of the liquid under analysis, incubating to develop a detectable response that is proportional to the concentration of the analyte under study, and detecting the response. In a preferred form, the response is detected by reflective scanning of the element through window 18 and the transparent support.

Thus, the detection is preferably accomplished radiometrically, but any form of detection is possible using this invention, including potentiometric detection, provided that the detecting means, hereinafter described in detail, is suitably modified. As used herein, "radiometric" and its derivatives are understood to include colorimetric as well as fluorimetric species.

The embodiments hereinafter described refer to blood serum as the preferred liquid under analysis. In addition, other analyte-containing liquids can be so analyzed, including industrial liquids containing non-biological analytes.

Descriptive terms such as "above", "below", "downward", "bottommost" and the like as used herein refer to orientations during use of the analyzer. The term "time-independent access" as applied to the incubator refers to its flexibility in accepting another test element at any time, rather than only when the next available one of several discrete incubator positions is aligned with the means for loading the incubator.

Figure 2:
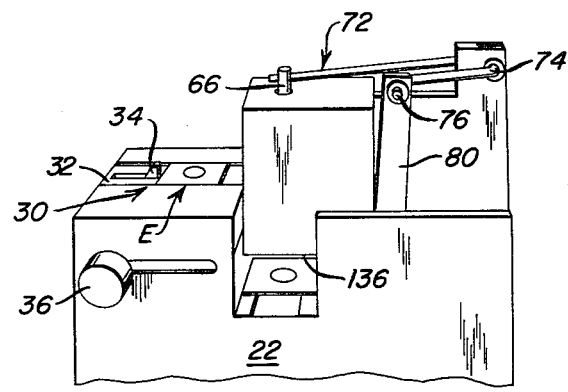
FIG. 2 is a fragmentary perspective view of an assembled analyzer.
Figure 3:
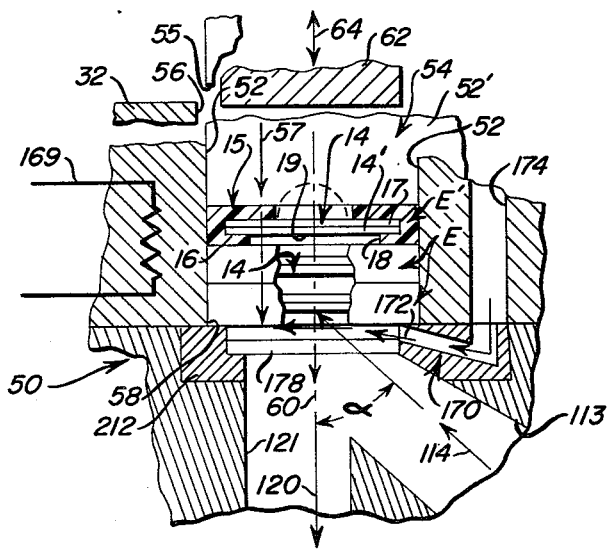
FIG. 3 is a fragmentary sectional view of the incubator of the analyzer, as seen from the ejector element side.

Referring to FIGS. 1-3 and FIG. 1 in particular, an analyzer 20 constructed in accordance with the invention comprises a frame 22 that mounts a test element loading means 30, a metering station 40, an incubator 50, a radiometer 110 as the detecting means, and test element unloading means 130. Loading means 30 comprises a platform 32 which is optionally preheated, a pusher finger 34 that projects up through a slot 35 in the platform and a handle 36 on which finger 34 is mounted. Platform 32 is preferably provided with conventional electrical heating elements, not shown, and is disposed between shoulders 38 that, in cooperation with finger 34, guide test elements E and E' in the direction of arrows 39 toward incubator 50.

Metering station 40 can incorporate any metering device for depositing a drop of test liquid onto element E or E' as it rests on platform 32. A preferred device is a pipette 42 mounted in a holder 44 so that tip 46 of the pipette is disposed closely adjacent and directly above portion 14 of the test elements. Preferably, tip 46 is disposable to prevent sample contamination of the remainder of pipette 42.

Alternatively, station 40 can be omitted and the liquid added to the elements by any other instrument, not shown, prior to being placed on platform 32.

In accordance with one aspect of the invention, an incubator 50 is provided in analyzer 20 with walls 52, FIG. 3, that define a generally elongated chamber 54. To permit test elements E and E' to be introduced into chamber 54 at a first location 56, wall 52 is provided with an access aperture 55, FIGS. 3 and 4, adjacent platform 32. Chamber 54 also includes an element-reading location 58. Within the chamber the elements follow path 57 from first location 56 to location 58, along the longitudinal axis 60 of the chamber. Walls 52 preferably are shaped to form a guide means or a rectangular chute the dimensions of which will accommodate the test elements in a sliding fit, with element portions 14 and 15 extending generally transverse to axis 60. Therefore, each test element in chamber 54 necessarily contacts the adjacent elements such that each support surface 16 of frame member 15, as well as of the support surface 19 of support 14', covers the sample-containing portion 14 of the element preceding it. More specifically, the length of the chamber between locations 58 and 56 will accommodate a continuous train of "n" elements, n being equal to three in the embodiment of FIG. 4. The element at location 58 is of course the first element of the train to have been inserted by loading means 30, and element E' is the last element of which portion 14 is not covered by the adjacent test elements.

Preferably, chamber 54 is disposed vertically, whereby the configuration of the incubated elements is that of a contiguous stack. Gravity is usually sufficient in such an embodiment to move the elements from location 56 to location 58. Also preferably, incubator 50 is stationary with respect to the other non-moving parts of the analyzer.

A cover 62 is preferably included for element E', FIGS. 1 and 3, since portion 14 of element E' is not otherwise covered. Because the cover has to be withdrawn if and when an additional element is added to chamber 54, it is mounted to reciprocate, arrows 64, within chamber 54 from a position above location 56 to a position in contact with either the bottom of the chamber at location 58 or the elements E in the chamber. Preferably cover 62 is secured to a rod 66, FIG. 1, that in turn is secured via connector means 67 to handle 36. Referring to FIGS. 2 and 4–6, connector means 67 comprises crank 72, pinioned at end 70 to rod 66. Crank 72 is J-shaped, the mid-portion 74 being journalled to frame 22 as a pivot point. End 76 of shorter leg 78 of crank 72 is then journalled to a link 80 that reciprocates vertically on the frame. One end 82 of link 80 is connected to crank 72, and the other end 84 rides on a camming bar 86 provided at one end 88 with a camming surface 90, FIGS. 4 and 6. Link 80 is confined to vertical movement by reason of end 84 being journalled to link arm 91, FIGS. 4 and 5, of frame 22. The opposite end 92 of bar 86 is journalled to handle 36, FIG. 6, and the entire bar 86 slides, arrows 94, within a V-shaped groove 96 of the frame. The opposite end 98 of handle 36 can be guided between two plates 100 for rotational stability.

Optionally, pusher finger 34 is mounted to rotate in the direction of arrows 102 on handle 36, with a torsion spring, not shown, biasing the finger back in the other direction. A sloping camming surface 104 on finger 34 permits elements E to be inserted by auxiliary means which override finger 34.

Preferably, cover 62 is given sufficient weight, due to its bulk, to serve as means for urging elements E through the chamber. That is, when shaped as a platen, cover 62 serves to prevent elements E from lodging against the walls 52. However, the urging capability of cover 62 is not needed if the spacing between walls 52 is enlarged to prevent accidental lodging of elements E.

In an alternate embodiment, not shown, cover 62 is omitted entirely, for example, in those analyzers that test for only those analytes that do not generate a gas as the detectable reagent and do not require a thermal cover.

Radiometer 110 is disposed at or adjacent to location 58, to read the bottommost element E in the chamber. Useful radiometers include colorimetric and fluorimetric radiometers such as are conventional in the art. A preferred form is a reflectometer comprising a light source 112 located generally underneath platform 32, FIG. 1, aligned at 45° to axis 60 to send light via radiation guide means 115, FIG. 1 through passageway 113, FIG. 3, in the direction of arrow 114 to the viewing window 18 of the bottommost element. A diffraction grating 116, FIG. 1, adapted to produce a spectrum of from about 340 to about 700 nm wavelengths, is disposed in the path of beam 120, and photodiodes or detectors 118 each are positioned to detect a particular wavelength of spectral beams 119, passed through a lens, not shown, as is conventional. The diffuse component of the reflected beam 120 is collected via radiation guide means 122, FIG. 1, through a passageway 121 aligned with axis 60, FIG. 3. Grating 116 is preferably telecentrically located, i.e., at the focal point of lens 122. The signals generated by detectors 118 are converted via an analog to digital convertor coupled to a conventional computer such as a microprocessor, not shown, to a concentration value based upon calibration values that have been manually keyed into the micro-processor. Optionally, the micro-processor also includes a timing device, not shown, that computes how long each test element is incubated prior to initiating the reading cycle.

Other radiometers are useful with the incubator described above. As one alternative, not shown, the plane defined by light beams 114 and 120 can be perpendicular to the plane defined by the spectral beams 119, with source 112 disposed under surface 133 discussed below.

Figure 4:
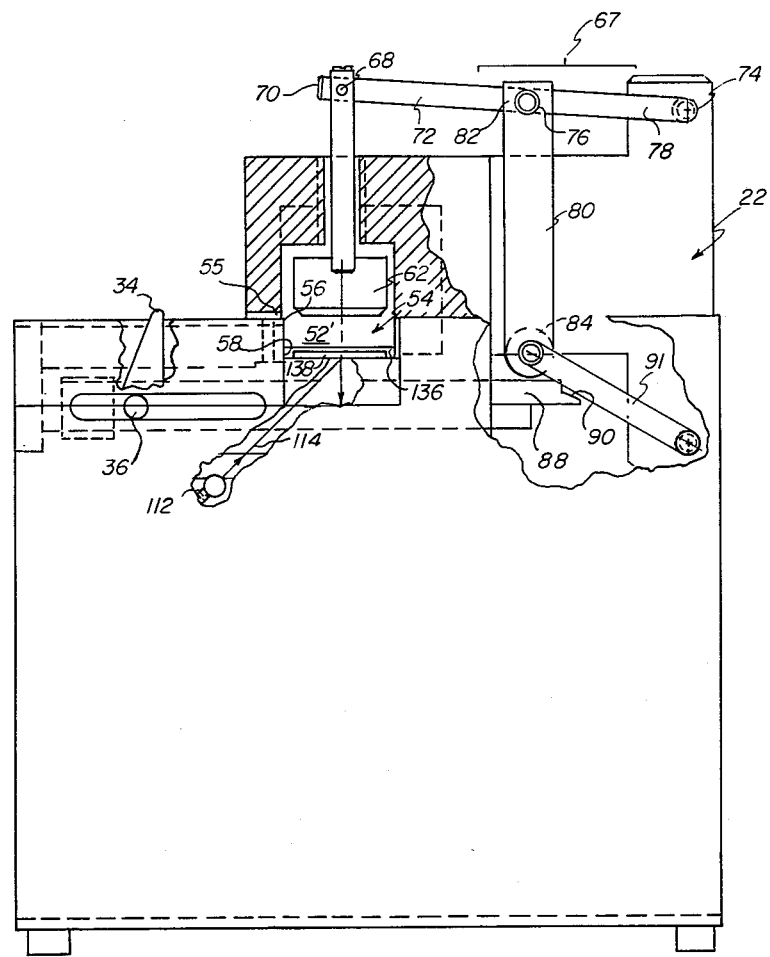
FIG. 4 is a fragmentary perspective view of the analyzer, in which the metering station has been removed for clarity.
Figure 5:
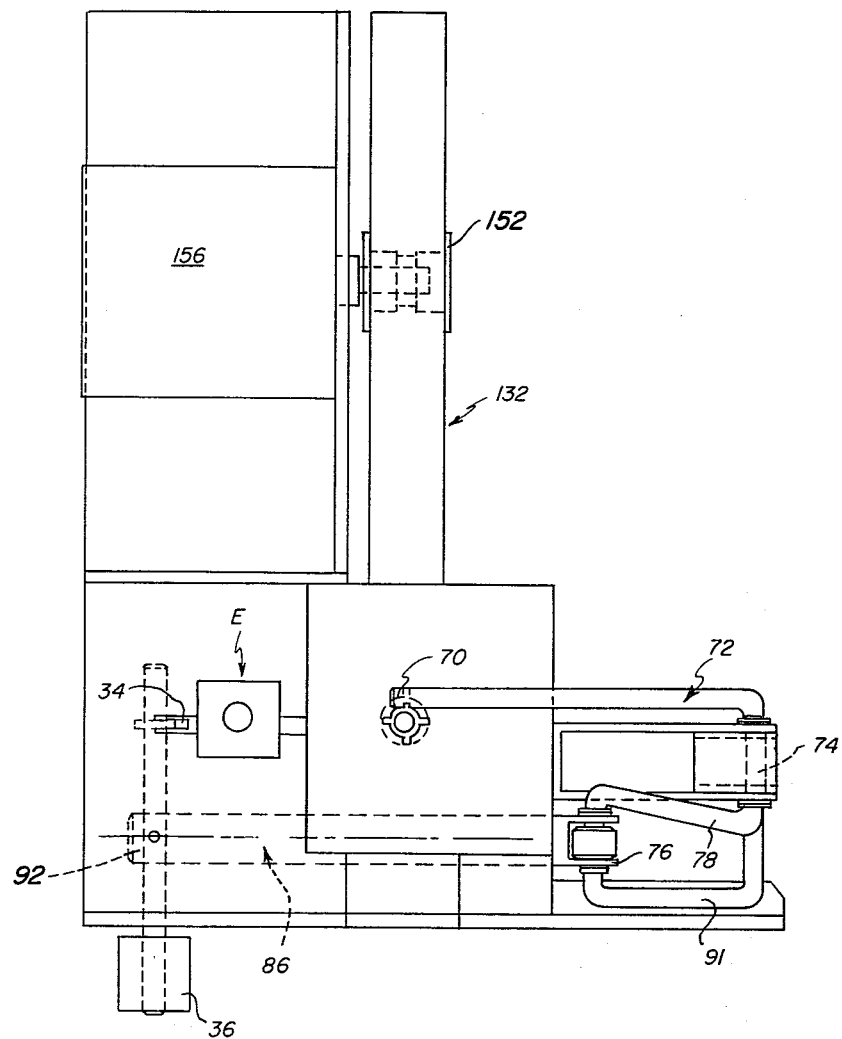
FIG. 5 is a plan view of the analyzer.
Figure 6:
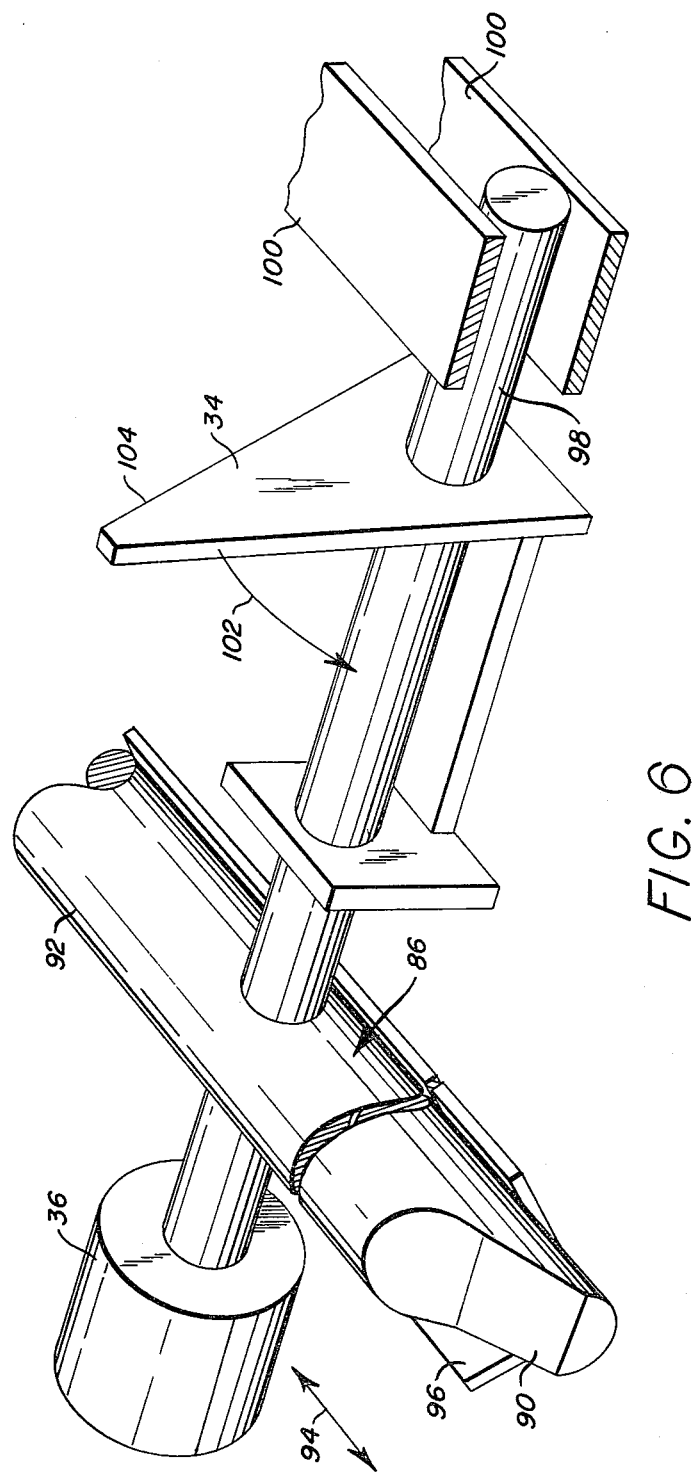
FIG. 6 is a fragmentary perspective view of part of the mechanism by which the urging means of the incubator is connected to the loading means.
Figure 7:
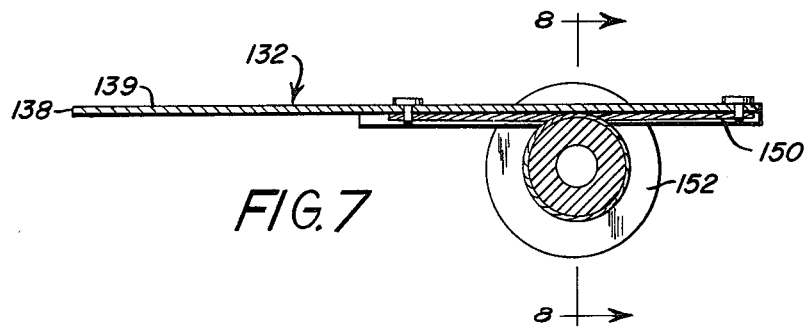
FIG. 7 is an elevational view of the ejector element of the unloading means, one flange of the spool being removed for clarity.

To sequentially unload incubator 50 on a first-in, first-out basis, unloading means 130 comprises ejector element 132 disposed at location 58 of chamber 54 to remove the read element E from the stack, across support surface 133 in the direction of arrow 134 out through aperture 136, FIGS. 2 and 4. Element 132 is an elongated blade having a pusher end 138, a top surface 139 and undersurface 140, FIGS. 7–9. The portion of undersurface 140 adjacent to end 138 is preferably provided with a white reference coating or standard surface 142 and a dark reference coating or surface 144, to calibrate the analyzer. Alternatively, the dark reference reading is obtainable by using a shutter or by extinguishing the light source, and the white reference reading is obtainable by a feed-back diode, not shown, that monitors or controls the intensity of source 112.

Figure 8:
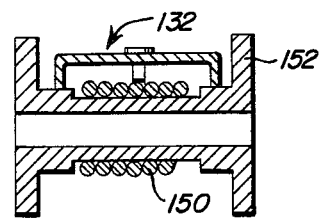
FIG. 8 is a sectional view taken generally along the line 8—8 of FIG. 7.
Figure 9:
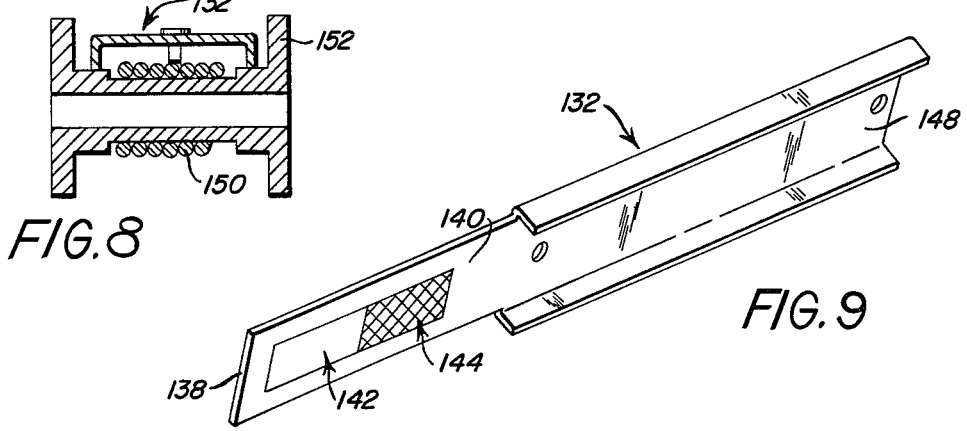
FIG. 9 is a perspective view of the ejector element.

The portion 148 of undersurface 140 of element 132 that is distal to end 138 is secured by means such as screws to a cable 150 that is wound upon a spool 152, FIG. 8. Rotation of the spool serves to reciprocate ejector element 132 in the direction of arrows 154, FIG. 1, as directed by a conventional A.C. reversible motor 156. One or more sensors 158, conventional opto-electric switches that cooperate with angle members 160, serve to control the operation of the motor. For more accurate control over the extent of travel of ejector element 132, for example as is desirable when radiometer 110 is located outside of the incubator as described hereinafter, a stepper motor is provided in place of motor 156, operatively connected to element 132 by a rack and pinion, wherein the rack is on the element 132.

Alternatively, end 138 of ejector element 132 can be bifurcated, not shown, so that it bears only on the edges of the test elements.

The dimensions for the parts described are not critical and depend upon several factors, of which the test element dimensions are a major factor. For example, for test elements that are about 24 mm by 28 mm, the walls 52 are set apart a distance that provides about 0.25 mm total clearance of the test elements for each of the single side edges 23 and 21 of the elements, to permit the sliding fit of the elements transverse to the longitudinal axis of the incubator. Alternatively, other sizes and/or shapes for the test elements dictate appropriate alterations in the size or shape of the chamber.

Regardless of the size of the test elements, for proper alignment of the viewing area of the element with the radiometer 110, at location 58 of the incubator, the outside dimensions of the test element preferably are maintained with close tolerances, i.e., no greater than ±0.25 mm. Alternatively, one of side walls 52 of incubator 50, and preferably the side wall 52′, FIG. 4, is used as a reference surface against which the test elements are biased when they reach end portion 58 of the incubator. To so bias the test elements, preferably the top surface 139, FIG. 7, of ejector element 132 is provided with a friction material, not shown, that engages the next test element to be viewed as the ejector element is being withdrawn from the incubator prior to the next reading by the radiometer. The friction material serves to pull the test element up against wall 52′. Small pads of urethane are representative of useful friction materials.

If such friction material is used, the ejector element is preferably fully extended into the incubator when the first test element E is inserted into the incubator. The test element E also is preferably biased by a movable finger, not shown, in the orthogonal direction against one of the walls 52, FIG. 3, that is perpendicular to wall 52′, not shown. Such finger is linked to the movement of ejector element 132 so as to clear chamber 54 when the unloading means is activated.

The operation of the analyzer will be readily apparent from the preceding discussion. A test element E is deposited on platform 32 where it is preheated and spotted with a drop of liquid by the metering station 40. Any size drop is useful, although it has been found that for test elements E described, 10 μl is a preferred volume. Following the metering operation, the operator pushes handle 36 towards incubator 50, causing pusher finger 34 to move element E towards chamber 54. At the same time, camming bar 86 causes link 80 to move rod 66 upwardly, clearing cover 62 from chamber 54. Element E is thus placed into the chamber, and the return of handle 36 to its initial position causes bar 86 to clear link 80 and thus cover 62 falls onto element E at location 58 of chamber 54. A period of incubation follows, during which the color density or other response, e.g., fluorimetric response, develops. During this time, additional elements E can be spotted with liquid and sequentially placed into chamber 54 in like manner. Any gas that might otherwise evolve from portion 14 of element E is trapped and confined by the covering relationship of the test element above it, or by cover 62 if the element is last element E′. The resulting pressure tends to retain the gas within the test element. Eventually, and in the same sequence in which the test elements are spotted, they are read by radiometer 110 and the signals are converted to a concentration read-out for recording by the operator. After detection by the radiometer, the elements are ejected or removed by ejector element 132. Each time ejector element 132 is activated to remove a test element, coating 142 and then coating 144, if present, are read by the radiometer to maintain proper calibration of the analyzer.

Optionally, incubator 50 includes temperature control means for maintaining walls 52 at a constant, predetermined, elevated temperature, for example, 37° C. A variety of conventional heating techniques are useful. For example, electrical elements 169, FIG. 3, are mountable within or in contact with walls 52. In such an embodiment, cover 62 is preferably a conductive metal so as to be passively heated by walls 52 or actively heated by electrical elements mounted therein. Such temperature control means are preferred when the detected analyte is markedly variable with temperature, for example, when the analyte is an enzyme.

An additional optional feature is a nozzle 170, FIG. 3, mounted at location 58 for directing an air stream in the direction of arrows 172 along the reading face of the bottommost test element E. Such a stream removes any moisture that might condense on the reading face as a result of evolved water vapor. Nozzle 170 is supplied, e.g., with air via a passageway 174 fed from the heated portions of wall 52. A transparent plate 178 is disposed far enough away from the support surfaces of elements E so that a Coanda air flow effect is created as the air stream attaches to the test element E being viewed.

Figure 10:
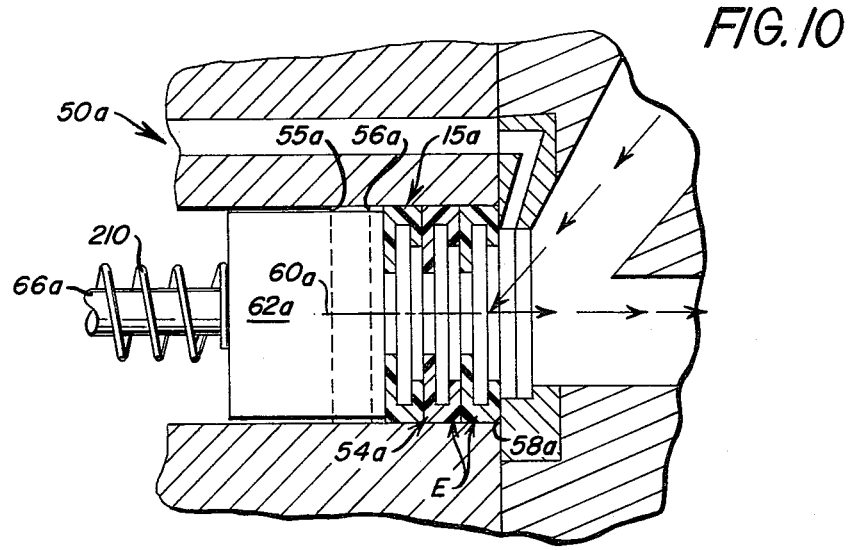
FIG. 10 is a sectional view similar to that of FIG. 3, but illustrating an alternate embodiment.

In FIG. 10, the incubator is depicted alternatively as comprising a chamber oriented horizontally rather than vertically as in the previous embodiment. Parts similar to those previously described bear the same reference numeral to which a distinguishing suffix "a" is attached. Thus, the analyzer comprises an incubator 50a having an elongated chamber 54a with a longitudinal axis 60a, and a radiometer as before. Test elements E are each inserted into chamber 54a in contact with the next adjacent element with frame members 15a extending generally transverse to axis 60a, also as before. However, the elements E are now inserted through a vertical aperture 55a, shown in dashed lines, and are maintained generally vertically as they move from location 56a to location 58a. The means urging the elements to move in this fashion is a cover 62a on a rod 66a biased by a spring 210 to move the cover towards location 58a. Rod 66a is caused to reciprocate in cooperation with the loading means by the same mechanism as is described for the previous embodiment, except that end 84 of link 80 is positively journalled to end 88 of bar 86. Ejection of read elements occurs as before.

The parts of the incubator and other described components are metallic or plastic as determined by conventional design considerations. If walls 52 and portion 212 of location 58, FIG. 3, are to be heated, then preferably they are metallic, such as copper, whereas the portions defining passageways 113 and 121 are preferably plastic to prevent heat loss.

In yet another embodiment, not shown, the radiometer is disposed outside of the incubator, to detect from below support surface 133, the response of each slide separately after it is ejected from the incubator. Such an arrangement of the detecting means is particularly preferred for test elements that are so transparent as to allow the adjacent elements to be sensed if the radiometer is located at the bottom of the incubator as previously described. In such an embodiment, a backing surface is disposed above the support surface, and preferably includes a white reference coating that is scanned when a test element is not present. The radiometer disposed outside of the incubator chamber directs a light beam up to the readable support portion of the element, at window 18 as the element is ejected along path 134.

The advantages of the analyzer of the invention will be readily apparent from the preceding discussion. Time-independent access of test elements is possible with a rapid through-put rate. No motor, gears, controls or rotation-permitting heating controls are necessary for the incubator itself, because the incubator is stationary rather than rotating. No addressing or computer tracking of addresses is necessary for proper retrieval of the elements in the incubator other than the conventional indexing device described above. Because no space is required between test elements, the size of the incubator is reduced to a minimum. Finally, control of evolved gases is provided by the arrangement of the test elements themselves, eliminating the need for special parts in the incubator chamber. The result is an analyzer that is particularly useful at, e.g., a doctor's office.

The invention has been described in detail with particular reference to certain preferred embodiments thereof, but it will be understood that variations and modifications can be effected within the spirit and scope of the invention.

What is claimed is:

1. In apparatus for the analysis of sample analytes using generally flat test elements having a first major surface that includes a sample-containing portion, and an opposing support surface, said apparatus including
   (i) an incubator capable of containing a plurality of said test elements,
   (ii) means for loading said test elements into said incubator at a first location, and means for unloading said test elements from said incubator at a second location, and
   (iii) means adjacent said second location for detecting a response in the incubated test elements;
   the improvement wherein said incubator includes means for (a) defining a path between said first and second locations, and (b) supporting a plurality of such elements for movement along said path with each element in contact with the adjacent elements and with the sample-containing portion of all but one of said elements being covered by said one or more support surfaces of an adjacent element.

2. Apparatus as defined in claim 1, wherein said defining and said support means comprises walls providing a chamber having a longitudinal axis disposed generally perpendicularly to the plane of the test elements in said chamber.

3. Apparatus as defined in claim 2, wherein said chamber contains said elements in a generally vertical stack.

4. Apparatus as defined in claim 2, wherein said unloading means includes an aperture in said walls at said second location sized to permit ejection of an element from said chamber, and an ejector element adapted to reciprocate into and out of said chamber to push a test element out through said aperture.

5. Apparatus as defined in claim 4, wherein said element includes as a surface facing said detecting means, a calibrating surface.

6. In apparatus for the analysis of sample analytes using generally flat test elements having a first major surface that includes a sample-containing portion, and an opposing support surface, said apparatus including
   (i) an incubator capable of containing a plurality of said test elements,
   (ii) means for loading said test elements into said incubator at a first location, and means for unloading said test elements from said incubator at a second location, and
   (iii) means adjacent said second location for detecting a response in the incubated test elements;
   the improvement wherein said incubator comprises wall means for defining a stationary, generally elongated chamber and, at said first location, an access aperture permitting introduction of elements into said chamber, said chamber being adapted to support a plurality of said test elements in a configuration wherein each element is in contact with adjacent test elements and the sample-containing portion of all but one of said elements is covered by said one or more support surfaces of an adjacent element.

7. In apparatus for the analysis of sample analytes using generally flat test elements having a first major surface that includes a sample-containing portion, and an opposing support surface, said apparatus including
   (i) an incubator capable of containing a plurality of said test elements,
   (ii) means for loading said test elements into, and means for unloading said test elements from, said incubator, and
   (iii) means for detecting a response in the incubated test elements;
   the improvement wherein said incubator comprises wall means adapted to receive and maintain a plurality of said elements in a contiguous stack, with said sample-containing portion of all but one of said elements being covered by said one or more support surfaces of an adjacent element in the stack;
   said detecting means and said loading means being disposed with said stack generally between them and said detecting means being positioned to detect the bottommost element of said stack, said unloading means being disposed adjacent said detecting means.

8. In apparatus for the analysis of sample analytes using generally flat test elements having a first major surface that includes a sample-containing portion, and an opposing non-sample-containing surface, said apparatus including
   (i) an incubator capable of containing a plurality of said test elements,
   (ii) means for loading said test elements into said incubator at a first location, and means for unloading said test elements from said incubator at a second location, and
   (iii) means for detecting a response in the incubated test elements;
   the improvement wherein said incubator includes guide means for guiding a plurality of such test elements in succession from said first location to said second location with each element being in contact with adjacent elements;
   said loading means being disposed to orient elements in said guide means such that the sample-containing portion of all but one element is covered by said non-sample-containing surfaces of an adjacent element.

9. Apparatus as defined in claim 8, and further including means for urging elements in said guide means into such contacting relation.

10. Apparatus as defined in claim 9, wherein said urging means includes a spring under compression.

11. Apparatus as defined in claim 1, 2, 6, 7 or 8, and further including means for covering said one element not covered by an adjacent element.

12. Apparatus as defined in claim 11, wherein said covering means includes a movable cover, and further including means operatively connecting said cover to said loading means to displace said cover away from said detecting means while additional elements are being loaded.

13. Apparatus as defined in claim 1, 6, or 7, and further including means for urging the test elements through said incubator towards said detecting means.

14. Apparatus as defined in claim 1, 6, 7 or 8, and further including means for maintaining said incubator at a predetermined temperature.

15. Apparatus as defined in claim 1 or 6, and further including means at said second location for directing an air stream across said support surface of each of said elements so that condensed moisture is removed prior to reading.

16. An incubator for an analyzer that detects sample analyte responses in generally flat test elements having a first major surface that includes a sample-containing portion, and an opposing support surface, the incubator comprising wall means structured to receive said test elements one at a time at a first location, said wall means (a) defining a path from said first location to a second location suitable for the removal of said test elements from said incubator, and (b) being configured to support the test elements along said path each in contact with the adjacent elements, the sample-containing portion of all but one element being covered by said support surfaces of an adjacent element, and means for maintaining said incubator at a predetermined temperature.

17. A method of detecting analytes of sample liquids by the generation of detectable responses in test elements each of which contains a quantity of one of said liquids in a sample-containing portion; the method comprising the steps of (a) sequentially placing the elements in a configuration wherein each element is in contact with the adjacent elements and the sample-containing portion of all but one of said elements is covered by a support surface of one of said adjacent elements;

(b) detecting said responses of said elements in the same sequence as they are placed in said configuration; and (c) removing said test elements from said configuration either before or after said detecting step.

18. In apparatus for the analysis of sample analytes using generally flat test elements having a first major surface that includes a sample-containing portion, and an opposing support surface, said apparatus including (i) a radiometer capable of detecting a response in a test element, (ii) an incubator capable of maintaining a plurality of test elements under controlled conditions prior to detection of said test elements by said radiometer, and (iii) means for loading said test elements into said incubator at a first location, and means for unloading said test elements from said incubator at a second location;

the improvement wherein said incubator includes means for (a) defining a path between said first and second locations, and (b) supporting a plurality of such elements for movement along said path with each element in contact with the adjacent elements and with the sample-containing portion of all but one of said elements being covered by said one or more support surfaces of an adjacent element.

19. Apparatus as defined in claim 18, wherein said defining and supporting means (a) and (b) comprise wall means adapted to receive and maintain a plurality of said elements in a contiguous stack.

20. Apparatus as defined in claim 18, wherein said radiometer is disposed outside of the incubator to detect said test elements when they are unloaded from said incubator by said unloading means.

* * * * *

UNITED STATES PATENT AND TRADEMARK OFFICE
CERTIFICATE OF CORRECTION

PATENT NO. : 4,303,611
DATED : December 1, 1981
INVENTOR(S) : Thomas C. Jessop

It is certified that error appears in the above-identified patent and that said Letters Patent are hereby corrected as shown below:

Col. 9, line 46, the part reading "in claim 1," should read --in claim 1 or claim 18--.

Signed and Sealed this

Thirty-first Day of January 1984

[SEAL]

Attest:

GERALD J. MOSSINGHOFF

Attesting Officer

Commissioner of Patents and Trademarks